US 6,384,083 B1

(12) United States Patent
Ludwig et al.

(10) Patent No.: US 6,384,083 B1
(45) Date of Patent: May 7, 2002

(54) USE OF ADAMANTANE AMINES OR STRUCTURALLY SIMILAR COMPOUNDS FOR COMBATING BORNA DISEASE VIRUS AND FOR THE PREVENTION AND TREATMENT OF AFFECTIVE DISEASES AND OTHER DISORDERS ASSOCIATED WITH BDV INFECTIONS IN HUMANS AND ANIMALS

(75) Inventors: Hanns Ludwig, Beerenstrasse 41, D-14163 Berlin; Detlef Dietrich, Haferkamp 4 F, D-30916 Isenhagen; Hinderk M. Emrich, Wilkeninghof 2, D- 30659 Hannover; Liv Bode, Berlin, all of (DE)

(73) Assignees: Hanns Ludwig, Berlin; Detlef Dietrich, Isernhagen; Hinderk M. Emrich, Hannover, all of (DE)

( * ) Notice: Subject to any disclaimer, the term of this patent is extended or adjusted under 35 U.S.C. 154(b) by 0 days.

(21) Appl. No.: 09/297,489

(22) PCT Filed: Oct. 23, 1997

(86) PCT No.: PCT/DE97/02455

§ 371 Date: Jun. 14, 1999

§ 102(e) Date: Jun. 14, 1999

(87) PCT Pub. No.: WO98/18457

PCT Pub. Date: May 7, 1998

(30) Foreign Application Priority Data

Oct. 30, 1996 (DE) .......................................... 196 44 998

(51) Int. Cl.$^7$ ............................................... A61K 31/13

(52) U.S. Cl. ......................... 514/662; 514/660; 514/661
(58) Field of Search ................................. 514/660, 661, 514/662

(56) References Cited

U.S. PATENT DOCUMENTS 4,148,896 A * 4/1979 Smith ....................... 514/235.2

FOREIGN PATENT DOCUMENTS

| DE | 4014672 | 11/1991 |
| DE | 19510189 | 9/1996 |
| FR | 6482 | 11/1968 |
| WO | 9428885 | 12/1994 |

OTHER PUBLICATIONS

Biosis Abstract, AN 1993:593192, Macchio et al., 1993.*
Medline Abstract, AN 96035626, Pereira et al., 1995.*
Medline Abstract, AN 95152486, Nickels, 1994.*

* cited by examiner

Primary Examiner—Russell Travers
Assistant Examiner—Shengjun Wang
(74) Attorney, Agent, or Firm—Norris, McLaughlin & Marcus

(57) ABSTRACT

The invention concerns the use of 1-adamantane amines (amantadines) or structurally similar compounds for combating borna disease virus infections and for treating affective diseases and disorders associated with borna disease virus infections in humans and animals. The use of these substrates results in rapid and lasting elimination of the symptoms and signs and in the suppression of the virus activity.

9 Claims, 3 Drawing Sheets

USE OF ADAMANTANE AMINES OR STRUCTURALLY SIMILAR COMPOUNDS FOR COMBATING BORNA DISEASE VIRUS AND FOR THE PREVENTION AND TREATMENT OF AFFECTIVE DISEASES AND OTHER DISORDERS ASSOCIATED WITH BDV INFECTIONS IN HUMANS AND ANIMALS

This application is a 571 of PCT/DE97/92455, filed Oct. 23, 1997, which claim the priority of German application 1964498.7, filed Oct. 30, 1996.

BACKGROUND OF THE INVENTION

The invention relates to adamantane amines or structurally similar compounds for combating the Borna disease virus and for the prevention and treatment of emotional diseases and other disorders associated with BDV infections in humans and animals.

Emotional diseases, in general, and depressions of different severities, in particular, are among the most widespread syndromes at the present time, at least in industrialized countries. It is estimated that, for example in Germany, approximately 5% up to possible 10% of the population suffer at least occasionally from depressive disease conditions. These conditions are not merely mild emotional upsets; they are diseases, which severely affect the afflicted and can make them unable to work and this, not only if the condition exists for a longer time. The suicide rate for endogenous, depressive patients at the present time is of the order of 20%, if medical help is not sought. Frequently therefore, prolonged in-patient treatments are unavoidable which, in turn, is a problem for the patient as well as for the general public.

In the case of a longer in-patient treatment, the danger of hospitalization exists for the patient. Moreover, society must make sufficient therapy places available, including suitable clinics and specially trained personnel. All this is also associated with high costs for the general public.

It is now known that not only man, but also animals can suffer from emotional disorders in a similar manner. Such disorders are known, for example, for horses, in which the syndrome expresses itself as a listless phase, which is associated with drowsiness, loss of energy and frequently with disorders of muscular coordination. This horse disease is associated with an activated Borna disease virus infection. In the extreme case, the diseased animal must be put to sleep in order to bring an end to its suffering.

Depressions are also treated with drugs. On the basis of different theories, an attempt is made to influence the nervous system and to improve the depressive symptoms. Various anti-depressive drugs can have a mood-elevating, psychomotor-activating, calming or anxiety reducing, etc. effect to different degrees. The mode of action of most of the drugs has been clarified only inadequately.

For example, tricyclic and tetracyclic drugs are in use. According to other therapeutic attempts, selective seratonin reuptake inhibitors (SSRI), monoamino oxidase inhibitors or noradrenalin reuptake inhibitors are administered therapeutically. Many drugs have relatively severe side effects, such as the danger of convulsions, tremors, nausea and vomiting, headaches, anxiety states, severe liver and kidney disorders, anemia, etc. Moreover, the anti-depressive effect is limited or subjectively not present in a number of patients.

There is therefore a great need for a more effective medicinal treatment, and moreover for one with fewer side effects, for the treatment of emotional disorders of different origin.

Recently, the Applicants were able to find virus proteins and genetic material of the Borna disease virus (BDV) in the blood samples of emotionally sick patients during an acute depressive phase. This genetic material comprised sheathed, non-segmented, single-strand RNA virus of negative polarity, which is known to initiate emotional and, in some cases, depression-like symptoms in animals. It was possible to isolate the infectious human BDV from the blood of patients with different intensities of emotional diseases (L. Bode in Curr. Topics Microbiol. Immun. 1995, 190, 103–130; L. Bode, W. Zimmermann, R. Ferszt, F. Steinbach, H. Ludwig, Nature Med. 1995, 1, 232–236; L. Bode, R. D ürrwald, F. A. Rantam, R. Ferszt, H. Ludwig, Mol. Psychiatry 1996, 1 (3): 200–212).

It may be assumed that a BDV infection, aside from other factors, such as possibly a genetic predisposition, could represent a factor in the initiation of emotional diseases, which are characterized, for example, by changes in the messenger material area of the limbic system and could represent other, especially cerebral, disorders.

The problem, on which the invention is based, consists therein that depressions in man and animals are to be treated medicinally, as effectively as possible, without significant compromising side effects. At the same time, any BDV infection present should, if possible, be suppressed effectively or eliminated. Moreover, BDV infections in man and animal in general are to be controlled.

SUMMARY OF THE INVENTION

In order to solve this problem, the invention provides for the use of adamantane amines or compounds of a similar structure.

The inventive use is indicated for the prevention and control of viruses of the Bornaviridiae family, especially Borna disease virus (BDV) infections and for the treatment of emotional disorders and other disorders associated with Borna disease virus infections in humans and animals.

The inventive use may also be indicated for the prevention and control of infections in humans and animals with other viruses of the order of Mononegavirales.

A negative antibody finding does not exclude a BDV infection and, with that, an indication for the inventive treatment.

Since the mechanism of the adamantane action has not yet been clarified, it cannot be stated with certainty whether the action is causative or indirect.

1-Adamantane amine belongs to the group of adamantanes. These are stable, colorless, crystalline, tricyclic compounds with a "cage-like" structure. In its spatial structure, adamantane (tricyclo(3.3.1.1$^{3,7}$)decane itself is similar to a diamond, is water insoluble and, for that reason already, pharmaceutically not usable.

(I)

There are, however, certain pharmaceutically usable adamantane derivatives.

From the PCT WO 94/28885, a plurality of adamantane derivatives are known, which are substituted in different positions. These derivatives are, in particular, alcohols and ketones but do not include amino-substituted derivatives.

Numerous antiviral, antibacterial, antimycotic and antitumor properties, which are not quantified in greater detail, are ascribed to these adamantane derivatives. Certain ketones are said to be usable against HIV and possibly other retroviruses.

The water-soluble salts of 1-adamantane amine or of 1-aminoadamantane (international name (INN): amantadine, $C_{10}H_{17}N$, MW 151.26), amantadine sulfate (II) and amantadine hydrochloride (III) have been known for about 30 years as pharmaceutical active materials.

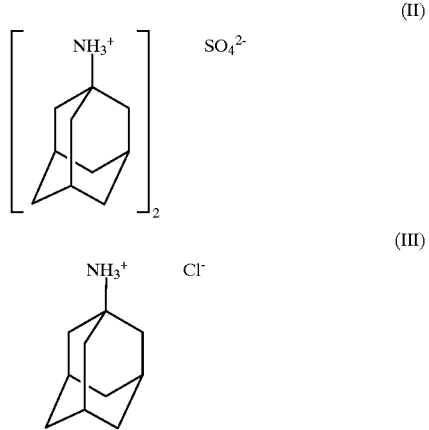

Amantadine sulfate or hydrochloride is still used at the present time for the treatment of Parkinson's disease and in the further area of the Parkinson syndrome in the case of an akinetic crisis, extrapyramidal disorders and reduced vigilance. As far as it is known, the pharmacological effect is based, among other things, on an increase in the availability of dopamine at the dopaminergic synapses. Details of the mechanism have not yet been clarified. On the basis of this effect on the nervous system, the use for the prophylactic treatment of migraines has also already being proposed (DE 19510189 A1).

Water-soluble amantadine derivatives were originally approved for the prophylaxis and treatment of certain influenza A strains. W. L. Davies, R. R. Grunert et al. (Science 1964, vol. 144, 862/863) discovered that amantadine hydrochloride inhibits the replication of viruses of four strains of influenza A and one of the C type. On the other hand, the closely related influenza B strains, mumps and a large number of other RNA and DNA viruses were not sensitive. In the case of the A strains, it was possible to push back the virus production by a power of 10, but it was not possible actually to suppress it. Amantadine sulfate and amantadine hydrochloride were thereupon approved internationally as a drug for the prophylaxis of influenza A infections and for the treatment of acute influenza diseases caused by influenza A viruses.

The specific activity of amantadine against influenza A virus is documented in vitro (cell culture) and on patients. The mechanism of action is based on the interaction of the substance with a membrane protein, $M_2$, which is specific for the influenza A virus and is thus specific for this virus. Influenza B viruses, which do not contain $M_2$ protein, are not sensitive. By means of the prophylactic administration, the frequency and degree of severity of virus influenza, caused by certain A viruses, are alleviated. If the substance is administered in the first 24 to 48 hours after the occurrence of the influenza symptoms, the duration of the illness can be shortened (R. Dolin, R. C. Reichman, H. P. Madore, R. Maynard, P. N. Linton, J. Webber-Jones, N. Engl. J. Med. 1982, 307, 580–584; W. L. Wingfried, D. Pollack, R. R. Grunert, N. Engl. J. Med. 1969, 281, 579–584); A. J. Hay et al., Embo. J. 1985, 4, 3021–3024; R. A. Lamb, S. L. Zebedee, C. D. Richardson, Cell 1985, 40, 627–633). The virostatic effect against influenza thus is limited.

The French FR 6482M discloses also 2-adamantane amines with a similar effect as alternatives for 1-adamantane amines for the treatment of influenza.

Because of the occurrence of amantadine-resistant influenza A strains (F. G. Hayden et al., N. Engl. J. Med. 1989, 121, 1696 to 1702) and the therewith associated danger, as well as the possibility of a protective vaccination for risk patients as alternatives, this area of indications of the drug (influenza) is practically no longer of any importance.

Surprisingly, it has now been discovered that amantadines show outstanding actions against Borna viruses. Here amantadines are understood to be primarily 1-adamantane amine or its pharmaceutically justifiable salts (such as amantadine sulfate, amantadine hydrochloride) as well as the 1-amino substituted, 1-alkylamino substituted or 1-aminoalkyl substituted adamantanes or their salts (such as N-1-adamantyl-2-((2-dimethylamino)ethoxy) acetamide=tromantadine, or 1-adamantyl-( 1-amino) ethane=rimantadine or their hydrochlorides or sulfates).

The outstanding anti-viral properties with respect to BDV are all the more surprising since chemotherapy of viral diseases is regarded in the literature as being generally very difficult, since a causal treatment always seems to be problematical because of the "use" of the metabolism of the host cell (Mutschler, "Arzneimittelwirkungen" (Drug Actions) WVG Stuttgart, $7^{th}$ Edition, 1996, pg. 725, 9.2.4).

Admittedly, it is known from the DE 39 21 062 A1 that 1-amantadine hydrochloride is said to be effective, however essentially only in combination with AZT, against HIV viruses by inhibiting viral replication. The cyto-protective effect, which is achieved according to DE 40 14 672 A1 with certain 1-adamantane amine derivatives, goes in a similar direction. However, it is a question here specifically of effects on retroviruses, which have a life cycle and manner or replication, which is completely different from that of Borna disease viruses.

The Borna disease virus, BDV, is a sheathed RNA virus of 90 Nm diameter, which has a non-segmented, single-stranded genome of negative polarity, which codes for five viral genes (T. Briese, A. Schneemann, A. J. Lewis, et al., Proc. Natl. Acad. Sci. USA 1994, 91, 4362–4366). Related viruses are, for example, the measles virus and the rabies virus. Because of its genetic peculiarities (replication in the nucleus of the host cell and not in the cytoplasm), the Borna virus is regarded as a prototype of its own virus family (Bornaviridae) within the order of Mononegavirales.

BDV was first known as a pathogenic animal virus, which can initiate episodic behavior disorder in animals. BDV strains from animals and humans are genetically very similar (more than 95% sequence homology!). BDV has a particular preference for nerve cells of the limbic system in the brain, which is responsible or co-responsible for behavioral control, emotions and memory performance (H. Ludwig, L. Bode, G. Gosztony, Progr. Med. Virol. 1988, 35, 107–151; Dittrich W. et al., Biol. Psychiatry 1989, 26, 818–828).

Presumably, due to the "activated" BDV infection, there are primarily functional disorders in the area of the brain messenger materials of this system (G. Gosztony, H. Ludwig, Curr. Topics Microbiol. Immun. 1995, 190, 39–73).

BDV infections do not destroy the host cell; they persist and are characterized by latent and activated phases. Especially during the activity phases, there may be symptoms of the disease.

Water-soluble derivatives of L-adamantane amines inhibit the infection with Borna disease virus (in vitro, to the extent of 80%) and prevent virus replication in the already infected cells. The extent of this effect, described in greater detail in the examples, is exceptionally high and completely unexpected. For the chemotherapy of viruses, such good virostatic results are unknown or very infrequent. The infection presumably was eliminated even completely (virus clearance, see below, Examples 2 and 3), this virocidal effect being totally surprising.

Furthermore, the materials, which are described here and claimed, act in vivo as a highly efficient therapeutic agents for emotional diseases and for disorders, which are related to BDV infections.

This effect is also extraordinarily and completely unexpected, especially in relation to the completeness of the elimination of the symptoms and the rapid response to the treatment (in this connection, refer particularly to Example 4). If the inventive amantadine is administered particularly during depressive episodes or during acute phases of other disorders associated with BDV infections, there is a clear and lasting improvement in the symptoms, such as has been observed with other therapeutic agents only in very rare cases, already after a few days.

Medication with inventive amantadines accordingly, in the narrower sense, is indicated for BDV-infected patients with mood disorders, especially in the depressive phase and, in the wider sense, for BDV-infected patients with disorders, which are correlated with BDV, such as, for example, functional disorders of the limbic system or functional temporal lobe disorders, chronic fatigue syndrome, anxiety disorders, compulsive disorders and schizo-mood psychoses.

According to DSM-IV, medication with amantadines is indicated especially for the following diagnosis numbers:

emotional disorders (mood disorders): 296.xx (particularly 296.3x, 296.5x, 296.6x, 296.7x, 296.8x, 296.90); 300.3; 300.4; 311; 293.83; 295.70; anxiety disorders, particularly in combination with a depression: 300.00; 300.02; 300.21; 300.22, and, according to ISD-10, for the following diagnosis numbers/categories:

mood disorders: F3 (especially F32, F33, F34, F38, F25); anxiety disorders: F41; compulsive disorders: F42.

The recommended dose for people is between 100 and 300 mg per day and preferably 200 mg per day or 0.01 to 6 mg per kg of body weight per day.

The duration of the treatment (curative), assumed at the present time to be meaningful, is 3 to 6 months.

The compounds, claimed pursuant to the invention, are also indicated for phase prophylaxis in the symptom-free interval for BDV-infected patients with the above-described disorders. The preventative administration of amantadines or corresponding effective materials is also indicated for healthy persons, who live in close domestic contact with BDV-infected patients (human or animal) and/or have a genetic risk for developing one of the above-described disorders.

The recommended dose for a prophylactic use is up to 200 mg per day and preferably 100 mg per day for a duration of about 1 to 3 months.

Basically, all forms of administration, which make absorption possible, come into consideration. For example, parenteral, intramuscular, subcutaneous, intradermal or topical. The oral administration in the form of a powder, (film) tablets, coated pills, capsules or the like is preferred. For certain applications, transdermal forms of administration, especially with a sustained release effect, such as a patch, come into consideration.

Amantadines generally are well tolerated. After oral administration, amantadine is absorbed almost completely. It is excreted in unchanged form through the kidneys. The half-lifetime is approximately 15 hours. For patients with renal insufficiency, preferably rimantadine is indicated, because it is metabolized in the liver and therefore the clearance of the drug does not depend on the function of the kidneys.

According to the present state of knowledge, the pharmacological action is ascribed essentially to the adamantane structure, although the mechanism is not yet known.

Therefore, water-soluble adamantane derivatives, such as the adamantane amines named above, or their pharmacologically justifiable salts, especially N-(1-adamantyl)amines and (1-adamantyl)alkylamines or their pharmacologically justifiable salts, basically are suitable for a treatment and prophylaxis in the sense of the invention.

Pursuant to the invention, amantadines can be used for the treatment of emotional disorders in people and animals. It is known, in particular, that horses, sheep, cattle and also cats can suffer from persistent Borna virus infections and then also show mood disorders, that is, symptoms of psychological illnesses. Depending on the load, especially BDV-infected horses are in danger of developing behavioral disorders with apathy as the main symptom and, without treatment, can become fatally ill, especially in the case of fulminant virus production.

The treatment of animals can also be indicated epidemologically, in order to inhibit BDV infections as a whole and to prevent the spreading of such infections. Since the mechanism of transfer of the virus is still unknown, such a treatment can also be regarded as a preventative method for maintaining human health.

Figure 1:
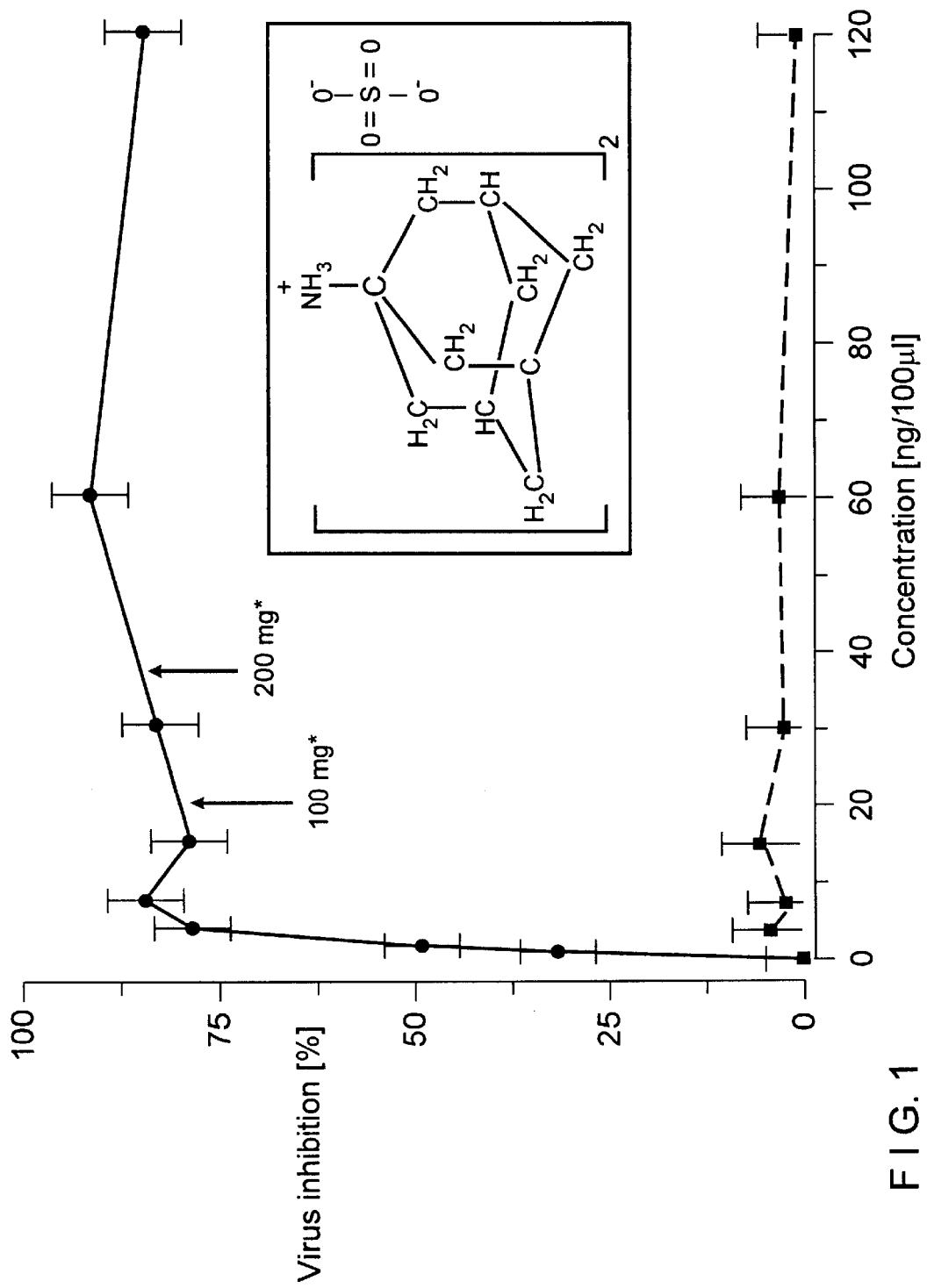
FIG. 1 Inhibition of a BDV Infection with Amantadine Sulfate in vitro
Figure 2:
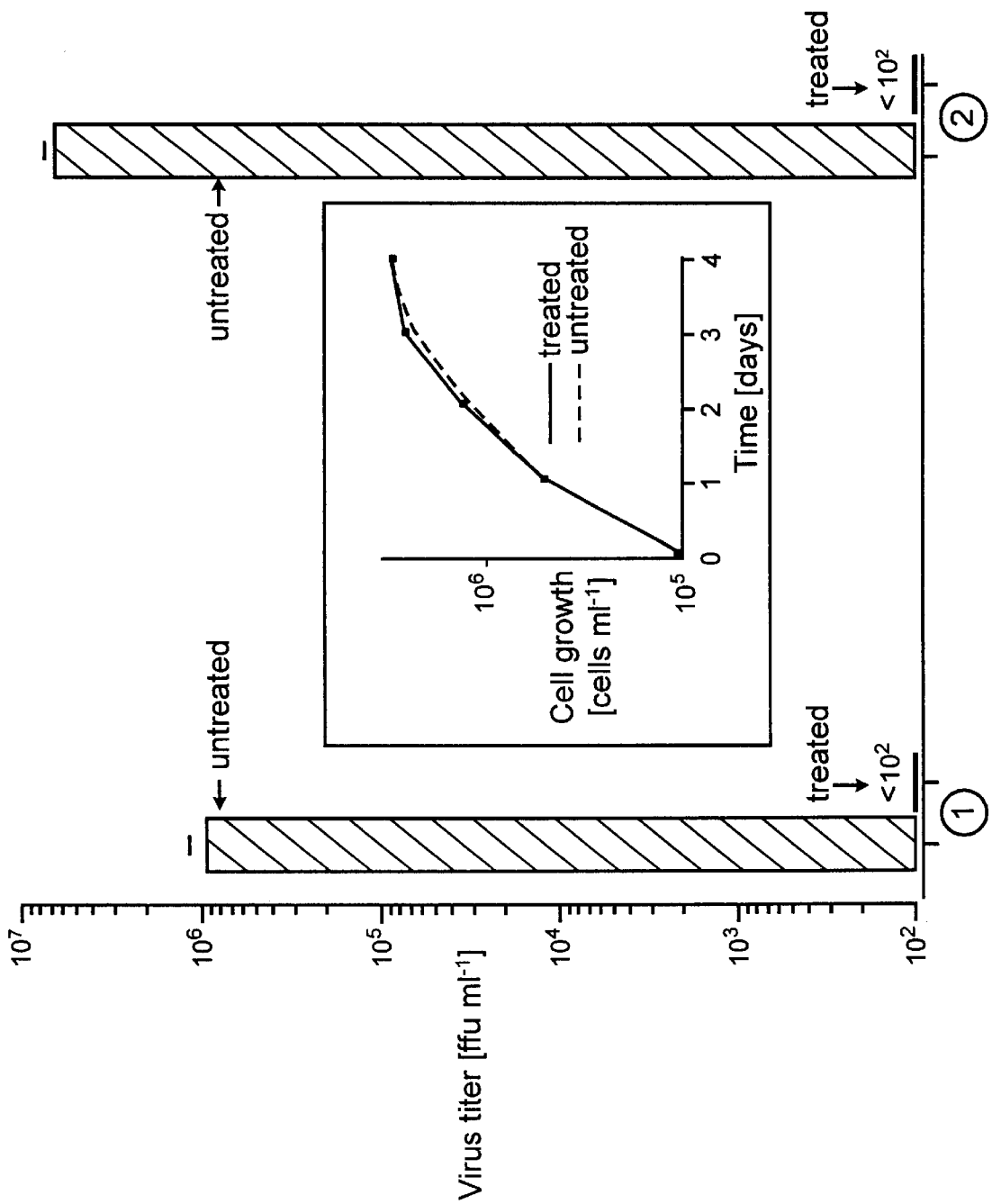

Treatment of rabbit brain cells either with amantadine sulfate (continuous line) or meso-inositol (broken line) for one hour before their infection (100±10 ffu/mL) with a human BDV strain (BDV-Hu1) * appropriate daily therapeutic dose of amantadine sulfate in mg, administered to the patient FIG. 2 Inhibition of BDV replication by amantadine sulfate Decrease in infectiousness 1) in human oligodendroglia (OL) cells, persistently infected with BDV-Hu-H1, which were treated for 6 days with 1.2 µg/mL of amantadine sulfate, and 2) in freshly infected OL cells, which were treated with the same dose for 24 hours before the infection and then for a further 6 days, in comparison with untreated control samples. faded in: cell growth of not-infected OL cells with (solid line) and without (broken line) amantadine sulfate (1.2 µg)

Figure 3:
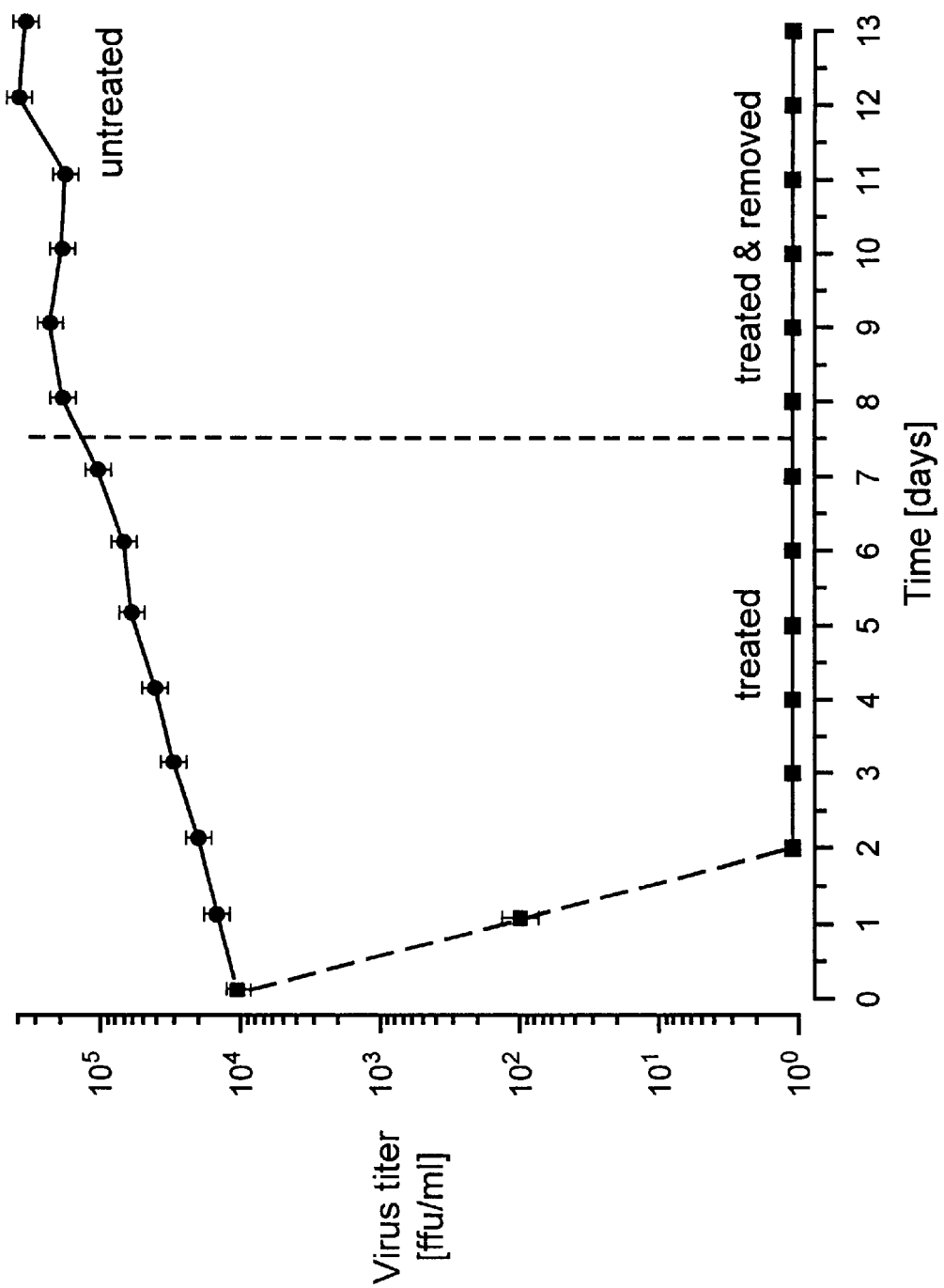

FIG. 3 Virus Clearance After Treatment with Amantadine Sulfate is Interrupted

Decrease in virus titer in a human oligodendroglia (OL) cell line, which was freshly infected with BVD-Hu-H1, treated for 6 days with 1.2 µg/mL of amantadine sulfate and subsequently kept untreated (broken line) for a further 8 days and subjected to daily passages (1:2) in comparison to freshly infected OL cells, which were, however, not treated over the whole period.

DESCRIPTION OF THE WORKING EXAMPLE

In the following, the invention is illustrated by means of example without limiting the universality.

EXAMPLES

Example 1

In Vitro

Young rabbit brain cells were treated with amantadine sulfate and, in a comparison experiment, with meso-inositol. After this treatment, both samples were treated for 1 hour with a human Borna disease virus strain (100±10 ffu/mL with BDV-Hu-H1 (regarding this strain, refer also to L. Bode, et al., Mol. Psychiatry 1996, 1(3), 200–212)).

After this one-hour pre-treatment, amantadine sulfate, at a concentration of only 0.019 μg/mL, inhibits the infection of rabbit brain cells with human BVD to the extent of 50%. The highest in vitro dose, which permits normal, unimpaired cell growth, is 1.2 μg/mL, relative to the cell system.

The dose of 100 to 200 mg daily, which is recommended for patients with a different indication (Parkinson's syndrome) and the tolerance to which has therefore already been well tested, corresponds to a level of 0.2 to 0.4 μg/mL, that is, to four-fold the dose, which is effective in vitro.

(In this connection, see FIG. 1)

Example 2

In Vitro

The inhibition of BDV application by amantadine sulfate was tested. For this purpose, human oligodendroglia cells (OL cells), persistently infected with BDV-Hu-H1, were treated for 6 days in vitro with 1.2 μg/mL of amantadine sulfate. On the other side, freshly infected OL cells were treated with the same drug dose for 24 hours and then for a further 6 days after the infection. Even in already infected human oligodendroglia cells, the number of infectious viruses was reduced by a factor of more than 10,000. The reduction in the virus titer to a level, at which BDV can no longer be detected, is reached already after 2 days. Over the whole of the period observed, the cell growth was practically not affected by the dose used of 1.2 μg/mL of amantadine sulfate.

(See FIG. 2)

Example 3

In Vitro

The treatment of oligodendroglia cells, infected with human BDV, with 1.2 μg/mL of amantadine sulfate in vitro was interrupted after 6 days for the following 6 days. The cells were subjected to passages every day. A BDV infection could no longer be detected even after the treatment-free interval. It can be concluded from this that not only the replication (reproduction) of BDV is prevented very efficiently in the presence of amantadine sulfate, but also that infected cells can be freed apparently permanently from the BDV infection by means of amantadines (virus clearance).

(See FIG. 3)

Example 4

In Vivo

In the case of a 67-year old female patient with a bipolar disease (DSM-IV: 296.53), which has existed for 11 years, and frequent stays in hospital because of manic and severe depressive episodes, an activated BDV infection was noted by detecting BDV proteins in leucocytes. The blood analysis was conducted 3 months after the start of a severe depressive episode, which had not improved significantly under conventional therapy (including mianserine and valproate).

Initially, the patient received 50 to 100 mg of amantadine sulfate daily on days 1 to 3, then 200 mg for 6 weeks followed by 100 mg for a further 12 weeks and then 200 mg again for 2 weeks, until further provisions are made. Her depression improved dramatically from the $8^{th}$ day to the $11^{th}$ day under the treatment. After the $15^{th}$ day, it was possible to discharge her from the hospital. After the $11^{th}$ day of the treatment, and also 5 months later, Borna virus activity (protein expression in the blood leucocytes) could no longer be detected. The patient merely showed a low antibody titer against BDV.

The therapeutic effect was greater and significantly more rapid than ever before for results achieved with conventional anti-depression drugs. According to psychological test methods and subjective findings, the symptoms of depression are no longer present since the dramatic improvement. Until now, there have been no undesirable side effects. The patient continues to do well.

According to this course of events, a prophylactic effect against manic phases also seems probable. Until 1993, an improvement in the depression of the patient was followed directly by the manic phase, that is, without a disease-free interval. In the last 3 years, depressive episodes with subsequent hypomanic rebound effects predominated. The longest symptom-free interval was 4 months. Under amantadine therapy, the patient has now been depression-free for 5 months without a hypomanic rebound effect.

What is claimed is:

1. A method for controlling viruses of the Bornaviridae family, comprising an administration to human and animals at a therapeutically effective dosage of up to about 10 mg/kg of body weight per day of adamantane amines against said viruses by a means selected from the group consisting of oral, parenteral, intramuscular, subcutaneous, intradermal and topical means.

2. The method of claim 1, wherein the viruses are the Borna disease virus in humans and animals.

3. The method of claim 1, wherein the adamantane amine is present in the form of a pharmaceutical salt.

4. The method of claim 1, wherein the adamantane amine is chosen from the group consisting of a 1-amino substituted, a 1-alkylamino substituted, a 1-aminoalkyl substituted adamantane, and a pharmaceutical salt thereof.

5. The method of claim 1, wherein the adamantane amine is a water soluble substance with the adamantane structure.

6. The method of claim 1, wherein the dosage is 1 to 4 mg/kg of body weight per day.

7. The method of claim 3, wherein the pharmaceutical salt is selected from the group consisting of amantadine sulfate and amantadine hydrochloride.

8. A method for the treatment of emotional diseases caused by Borna disease virus infections in humans, comprising administering a therapeutically effective amount of adamantane amines to the humans.

9. The method of claim 8, wherein the emotional diseases are bipolar disorders.

* * * * *